United States Patent [19]

Gueritee

[11] 4,110,324

[45] Aug. 29, 1978

[54] NICOTINIC DERIVATIVES OF ESTRIOL

[76] Inventor: Nicolas Guéritée, 65, rue des Vignes, 75016 Paris, France

[21] Appl. No.: 736,931

[22] Filed: Oct. 29, 1976

Related U.S. Application Data

[63] Continuation-in-part of Ser. No. 551,151, Feb. 19, 1975, Pat. No. 4,042,581.

[30] Foreign Application Priority Data

Feb. 26, 1974 [GB] United Kingdom ............... 08712/74

[51] Int. Cl.$^2$ ............................................. C07J 43/00
[52] U.S. Cl. .................................. 260/239.5; 424/241
[58] Field of Search ........................... 260/397.5, 239.5

[56] References Cited

U.S. PATENT DOCUMENTS

| | | | |
|---|---|---|---|
| 3,057,856 | 10/1962 | Zirm et al. ......................... | 260/239.5 |
| 3,336,347 | 8/1967 | Engelfried et al. ............... | 260/397.5 |

OTHER PUBLICATIONS

J.A.C.S. (1956), Mar. 20, by Norman et al., pp. 1152, 1155.

*Primary Examiner*—Elbert L. Roberts
*Attorney, Agent, or Firm*—Haseltine, Lake & Waters

[57] ABSTRACT

Nicotinic estriol derivatives, having hypolipidemic activity, are described.

3 Claims, No Drawings

NICOTINIC DERIVATIVES OF ESTRIOL

This is a continuation-in-part of U.S. Patent Application Ser. No. 551,151, filed Feb. 19, 1975 now U.S. Pat. No. 4,042,581.

This invention is concerned with a new class of estriol derivatives, as new industrial products, defined by the following general formula

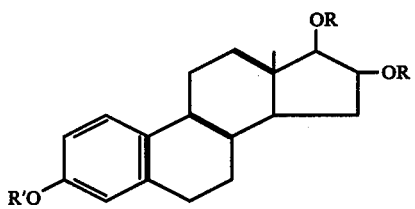

in which R is chosen from the nicotinoyl radical and its N-oxide and R' is an aliphatic organic acid residue containing from 3 to 7 carbon atoms or an aromatic, alicyclic or heterocyclicorganic acid residue or a methyl, ethyl, propyl, allyl, methallyl or cyclopentyl alcohol residue, as well as, in the case of a nicotinoyl residue, its N-oxide.

As non restrictive examples of compounds, accordin to the invention, Table 1 below lists 11 of them with their melting points.

TABLE 1

| Compound No | Code No | R' | R | Melting Point (° C) |
|---|---|---|---|---|
| 1 | 1B 032 | —CH₃ | nicotinoyloxy | 85° – 90° |
| 2 | 1B 080 | —CH₃ | N-oxide nicotinoyloxy | 152° |
| 3 | 1B 113 | —CH₂—CH=CH₂ | nicotinoyloxy | 72° |
| 4 | 1B 101 | —CH₂—CH=CH₂ | N-oxide nicotinoyloxy | 125° |
| 5 | 1B 062 | (cyclopentyl) | nicotinoyloxy | 135° – 140° |
| 6 | 1B 104 | (cyclopentyl) | N-oxide nicotinoyloxy | 251° |
| 7 | 1B 031 | —CH₃—CH₂—CO | nicotinoyloxy | 80° |
| 8 | 1B 356 | —CH₃—CH₂—CO | N-oxide nicotinoyloxy | 132° |
| 9 | 1B 029 | nicotinoyloxy | nicotinoyloxy | 110° – 115° |
| 10 | 1B 056 | N-oxide nicotinoyloxy | N-oxide nicotinoyloxy | 252° |
| 11 | 1B 317 | —CH₂—CH₂N(C₂H₅)(C₂H₅) | nicotinoyloxy | — |

The invention is also concerned with a process for obtaining these compounds from estriol, method consisting, in cases where the substitution at position C₍₃₎ is an etherification, in firstly performing this etherification, then in substituting the remaining hydroxyls in positions 16α and 17β, by acylation with nicotinoyl chloride, or the N-oxide of nicotinoyl chloride and, in cases where the substitution in position C₍₃₎ is an esterification, in directly performing the substitution of the hydroxyls in positions C₍₃₎, 16α and 17β, then, eventually, in selectively hydrolyzing the ester function at C₍₃₎ and undergoing another acylation at C₍₃₎ with a different acyl residue. The N-oxides can also be obtained from the oxidation of the corresponding amines by a per-acid, such as paranitroperbenzoic acid.

The following are examples illustrating the various methods.

EXAMPLE NO. 1

Preparation of 3, 16α, 17β-tricotinoyloxy, 1,3,5(10)-estratriene or "IB 029"

In a 100 cc flask, protected from light and humidity, 5.76g (0.02 Mole) of estriol are dissolved in 60 cc of anhydrous pyridine; 9.87g (0.07 mole) of nicotinoyl chloride are added and the whole shaken at 60° C for 6 hours. After cooling, the reaction mixture is poured into a liter of ice water and shaken for 15 minutes. The precipitate is dried and washed with water until neutral. Yield: 95%. The precipitate can also be extracted with chloroform or ether.

EXAMPLE NO. 2

Preparation of 3,16α, 17β-tricotinoyloxy, 1,3,5,(10)-estratriene N-oxide or "IB 056"

In a 100 cc flask, protected from light and humidity, 5.76g (0.02 mole) of estriol are dissolved in 60 cc of anhydrous pyridine. 10g of nicotinoyl N-oxide chloride are added and the whole shaken for 20 hours at room temperature. One liter of cold water is added and shaken for 30 minutes. After extraction with chloroform, the solution is dried over sodium sulphate and the organic solvent distilled off under reduced pressure. The crude product thus obtained is purified by chromatography on silica gel by eluting with chloroform and then with chloroform containing increasing quantities of methanol.

EXAMPLE NO. 3

Preparation of 3-propionyloxy, 16α,17β-dinicotinoyloxy,1,3,5 (10)-estratriene or "IB 031"

16α,17β-dinicotinoyloxy estriol is first prepared by partial hydrolysis of 3, 16α,17β-trinicotinoyloxy derivative (or "IB 29"). Protected from light and humidity 4g of 16α, 17β-dinicotinoyloxy estriol are dissolved in 40 cc of anhydrous pyridine. Then 2 cc of propionyl chloride are added at room temperature. It is shaken for 24 hours and then diluted with one liter of cold water. The precipitate is dried and washed until neutral with distilled water. It is then dried in vacuo in the presence of phosphoric anhydride.

EXAMPLE NO. 4

Preparation of 3-propionyloxy, 16α,17β-dicotinoyloxy,1,3,5 (10)-estratriene di-N-oxide or "IB 356"

1.6g of paranitroperbenzoic acid in a solution of 160 cc of chloroform are added to 1g of 3-propionyloxy, 16α,17β-dicotinoyloxy, 1,3,5(10)-estratriene in a solution of 155 cc of chloroform at 0° C. After shaking for 48 hours at room temperature, the reaction mixture is purified by chromatography on silica gel by eluting with a chloroform-methanol (90-10). The N-oxide obtained crystallizes from ether. Yield: 60%; melting point: 132° C. (Kofler).

EXAMPLE NO. 5

Preparation of 3-methoxy, 16α,17β-dinicotinoyloxy,1,3,5(10) estratriene N-oxide or "IB 080"

4g of 3-methoxy estriol are distilled in 60 cc of anhydrous pyridine in a 100 cc flask, protected from light and humidity. Then 6g of nicotinoyl N-oxide chloride are added in the solution which was previously cooled to 0° C. The whole is shaken overnight at room temperature and the reaction mixture is then diluted with 1 liter of ice water and extracted with chloroform. The crude product obtained is purified on silica gel with chloroform and then with chloroform containing increasing quantities of methanol.

EXAMPLE NO. 6

3-Cyclopentyloxy-16α,17β-dinicotinoyl-1,3,5,10-estratriene a. Preparation of the 3-cyclopentyl ether of estriol. In a 250 ml flask equipped with a cooler is dissolved:
1.750g of KOH in 75 ml ethanol.
This solution is added to the solution 2.88g of estriol. The mixture is heated under reflux for 15 minutes.
To this mixture is then added 3 cc of cyclopentyl bromide in 3 portions and refluxing for 30 minutes after each addition.

The mixture is then concentrated to 10–15 cc and 100 cc $H_2O$ are added. After stirring for 5–10 minutes, the mixture is dried, washed with NaOH N/10 then with water until neutrality.

After drying under vacuum at 40° C., 3.2g of the product (yield: 90%) is obtained.

After recrystallization from a mixture of ethanolhexane, there is obtained 2.5g of product (yield: 90%).

b. Preparation of the product of the invention:
In a vial, protected against the light, is dissolved: 2.5g of 3-cyclopentyl ether of estriol obtained in (a) above, in 25 cc of anhydrous pyridine.

There is then added, dropwise, 2.5g of nicotinoyl chloride, and after shaking for 2 days, the mixture is poured onto 500g of ice water.

After 10 mixutes of drying, the product is washed with water until neutral, then dried at 40° under vacuum. 4.1g of product is obtained.

To purify said product, it is dissolved in methanol, then treated with carbon black and then filtered and chilled overnight at 0°–5° C. After drying 2.3g of product, (yield: 56%), is obtained.

Preparation of the di-N-oxide of the above product:
In a vial protected against the light, is added: 3.5g of the product obtained above and 71.2 cc of anhydrous pyridine.

After shaking until complete dissolution, it is added 7.76g of nicotinoyl chloride N-oxide and the mixture is stirred for 20 hours at room temperature. Then the mixture is poured onto ice water and stirred for 30 minutes. After extraction with $CHCl_3$ and salting out with NaCl, the chloroform solution is washed with water until neutrality, dried over sodium sulfate and the organic solvent is removed under reduced pressure. The thus obtained product is purified by chromatography on silica gel the eluate is concentrated and the resulting compound is recrystallized.

Due to their new properties in comparison with the compounds from which they derive (estriol and nicotinic acid), the invention also relates to the application of the new compounds in human therapeutics as hypolipidaemics, in particular.

The hypolipidaemic effects of estriol are revealed significantly only at doses which inevitably lead to often undesirable hormonal responses.

The hypolipidaemic activity of nicotinic acid is only revealed from doses of roughly 1 gram per day at which point neurovegetative side-effects are quite frequent.

The substitution of at least two nicotinic residues at the 16α and 17β alcohol functions of estriol, according to this invention, as a consequence, multiplies the hypolipidaemic properties of nicotinic acid by a factor varying from 100 to 1000, with a concomitant decrease in the hormonal activities of the original estrogen. The compounds of the series claimed by this invention, effectively maintain the hypolipidaemic activities of nicotinic acid but, for the most active of them, at doses to the order of a microgram per kilo of body weight in both laboratory animals and humans, while maintaining the hypolipidaemic effects particular to estriol which are qualitatively different from those of nicotinic acid. These findings are most surprising and unexpected. Thus, the new compounds, as described by this invention, are very active in the treatment of human hyperlipidaemia and arteriosclerosis at doses where the side-effects of both the original substances cannot be revealed.

According to the invention, due to the N-oxidation of the two (or three) nicotinic residues of the compound, the invention relates, moreover, to the discovery of the power to reveal or to increase the hypolipidaemic properties by the oral route, while decreasing the estrogenic activities which could have subsisted after esterification. Thus, there is an additional increase in the therapeutic margin of these compounds, always to the advantage of the hypolipidaemic activity.

Lastly, the nature of the substitution at the phenol function ($C_{(3)}$), as defined above, which in itself is not original, enables the modulation of the intensity of the estrogenic effects of the nicotinic esters, according to the invention; this is very useful as it corresponds to various types of hyperlipidaemic patients. Thus, the nature of the substitution can:

a. either not influence estrogenic activity which thus remains analogous to that of estriol: this is the case of methyl ether ("IB 032") and allyl ether ("IB 113");

b. increase it by different routes of administration and different species: this is the case of cyclopentyl ether ("IB 062") and nicotinic triester ("IB 029");

c. or increase it considerably, but only the injectable route: this is the case of propionic ester ("IB 031").

The quantitative results compiled in Table II come from numerous experiments on estriol and the claimed compounds listed in Table 1.

The estrogenic effect (cornification of the vaginal epithelium) was determined after the single administration of the test-product (orally or s.c.) to ovariectomised rats weighing 100g(EMMENS, C. W., "Estrogens" in R. DORFMAN "Methods in Hormone Research", lind. vol. Part A. 2nd chapter; 1969 Acadmic Press).

The hypolipidaemic activities were determined subcutaneously on hyperlipaemia induced by an i.v. injection of Triton (WR 1339) to male rats (GARATTINI, S., et alia in "Drugs Affecting Lipid Metabolism", p. 144, Elzevier Publ. Co. 1961). All the figures of the first three columns represent the percentage of the effect produced subcutaneously by the standard (estrone).

The figures of the last column show the ratio between the hypolipidaemic activity and the estrogenic activity of each compound; the two figures indicated correspond to lipid parameters which responded the least ("minimum") or the most ("maximum") to the test products.

This way of expressing results enables the practical interest of an estrogen derivative to be predicted: this interest is in correlation with the opposition between the hypolipidaemic effects (+ +) and the hormonal activites (— —). Amongst the most currently used estrogens in therapeutics, estriol possesses the most important dissociation (COOK D. L. et alia Arch Int. Pharm. 1962 135:91-104). Now the compounds relating to the present invention significantly improve the effects of estriol in this respect. Thus, for an analogous hypolipidaemic effet, the estrogenic activity, for instance, of compound IB 080 is, according to the various parameters, 20 to 100 times weaker than that of estriol (cg. Table II).

TABLE II

| | N-Oxide | Percentage of cornifying activity (s.c. estrone = 100) | | Percentage of hypolipidaemic activities (s.c. estrone = 100) | | Ratio between hypolipidaemic and estrogenic activities of the compounds | |
|---|---|---|---|---|---|---|---|
| | | s.c. | oral | maximum | minimum | maximum | minimum |
| IB 032 | | 5.6 | 12 | 62 | 1 | 12 | 0.02 |
| | IB 080 | 3.5 | 3.5 | 1300 | 800 | 380 | 240 |
| IB 113 | | 13.2 | 6.2 | 100 | 0.5 | 80 | 0.4 |
| | IB 101 | 6.2 | 7.1 | 1600 | 5 | 240 | 0.8 |
| IB 062 | | 19;22 | 9;22 | 600 | 14 | 30 | 0.7 |
| | IB 104 | 13.5 | 33 | 400 | 22 | 280 | 1.6 |
| IB 029 | | 22;25 | 6 | 580 | 10 | 28 | 0.48 |
| | IB 056 | 7 | 6 | 1700 | 100 | 260 | 14 |
| IB 031 | | 65;38;40 | 12;2.3 | 180 | 10 | 13.8 | 0.2 |
| | IB 356 | 4 | 8 | | | | |
| IB 317 | | 0.07 | <0.05 | ≈40 | 0 | | |
| ESTRIOL | | 8 | 9 | 350 | 10 | 14.5 | 1.4 |

The hypolipidaemic activities of the compounds relating to this invention, differ considerably from those of classical estrogens from the double quantitative and qualitative points of view: estrone, estradiol and Premarin are effective on hyperlipaemia induced in rats by Triton at a dose of 75µg/kg/day, whilst the compounds relating to this invention (IB 080, for instance) are already very active at a dose of 3µg/kg/day (for the record, when using the same method, the effective dose of clofibrate is 300 mg/kg/day, thus 100,000 times greater).

Another method uses the plasma lipid variations of normal, intact rats treated daily (orally of subcutaneously) for several weeks with the test-product: a certain number of animals form each batch are sacrificed each week; the total lipids, cholesterol, triglycerides and phospholipids of the plasma are determined (UCHIDA K. et alia Endocrinol. Jap 1969 16:211; THEVENOT R. and HAZARD M. C. C. R. Solc. Biol. (Paris) 1973, 167:509).

As can be seen from the following tables (III A and III B) the activity of compound IB 080, as well as that of estriol, becomes significant from a doses of 0.6µg/kg/day against more than 75µg for estrone and estradiol; moreover contrary to what happens in the last two mentioned substances there is no attenuation nor inversion of the effects with the continuation of the treatment with IB 080 or estriol.

TABLE III

Variations of plasma lipides under the effect of various steroids. Spontaneous lipaemia
Male adult rats; s.c. route

TABLE III A
1st Experiment

| Day of sacrifice | LIPIDS VIII° | LIPIDS XV° | LIPIDS XXII° | TRIGLYCERIDES VIII° | TRIGLYCERIDES XV° | TRIGLYCERIDES XXII° | CHOLESTEROL VIII° | CHOLESTEROL XV° | CHOLESTEROL XXII° | PHOSPHOLIPIDS VIII° | PHOSPHOLIPIDS XV° | PHOSPHOLIPIDS XXII° |
|---|---|---|---|---|---|---|---|---|---|---|---|---|
| Controls (excip.: μg/ml) | 3, 91 | 3, 22 | 3, 56 | 1, 19 | 0.75 | 0, 71 | 1, 25 | 1, 145 | 1, 04 | 2, 20 | 1, 925 | 1, 52 |
| 3 | — | −9% | −29%° | — | −17%° | −64%° | — | −24%° | −10%° | — | −27%° | −10% |
| $E_3$(μg/kg/day) 15 | −24%°° | −21%°°(o) | −28%°° | −60%(o) | −41,5%(o) | −30% | −21%°° | −36%°(o) | −21%°(o) | −29%° | −26%° | −22% |
| 75 | −38%° | −28%°(o) | −39%°° | −66,5%° | −57,5%° | −35% | −39%°° | −37%°° | −34%° | −35,5%° | −43%°° | −19% |
| 15 | −17%° | +8% | −1,4% | −70,5%° | +64% | −35% | −5% | +8,5% | +34% | −19,5%°° | +4% | +38% |
| $E_2$(μg/kg/day) 75 | −14,5%° | +11% | −6% | −65,5%° | +16% | −10% | −17,5%(o) | −17% | +17% | +11, 5% | 0 | +12% |
| 15 | −6,5% | +2,5% | −15%(o) | −59%° | −8% | +15,5% | −3% | +26% | −13, 5% | −3, 5% | −13%(o) | −6% |
| $E_1$(μg/kg/day) 75 | −2,5% | +12,5% | −14,5%°° | −68,5%° | +4% | −45% | +3% | +10.5% | −4% | −12%(o) | +13% | +12% |

TABLE III B
2nd Experiment

| | VIII° | XV° | XXII° | VIII° | XV° | XXII° | VIII° | XV° | XXII° | VIII° | XV° | XXII° |
|---|---|---|---|---|---|---|---|---|---|---|---|---|
| Controls (excip.: μg/ml) | 4, 72 | | 4, 16 | 0, 88 | | 0, 635 | 1, 46 | | 1, 23 | 2, 34 | | 2, 04 |
| 0.6 | −5% | | −22%° | −68%°°° | | −39, 5%° | −7,5%° | | −10%° | −6% | | −23%°° |
| $E_3$(μg/kg/day) 3 | −12% | | −21%°° | −62,5%°° | | −51%°° | −13%° | | −14%° | −14%°° | | −26%°°° |
| 15 | −24% | | −22%°° | −59% | | −60%°°° | −21%°° | | −29%°°° | −17%°° | | −42%°°° |
| IB 080 0.6 | −15,5%(o) | | −11% | −60%°° | | −42%°° | −7,7%° | | −13%°° | −2% | | −36%°°° |
| expressed as 3 | −23%° | | −20%°° | −61%°°° | | −61%°°° | −11%(o) | | −25%°°° | −11% | | −45%°°° |
| $E_3$(μg/kg/day) 15 | −33% | | −24%°° | −74%°° | | −57,5%°°° | −25,8%°° | | −28%°°° | −23%°°° | | −45%°°° |

$E_1$ = estrone;
$E_2$ = estradiol-17β;
$E_3$ = estriol;
(o) = p = 0.05;
° = p < 0.05;
°° = p < 0.01;
°°° = p < 0.001

Table IV below confirms the quantitative and qualitative differences which exist between estriol and its derivatives of the series described by the present invention (here IB 080), on the one hand, and on the other the classical estrogens: even at a daily dose of 75µg/kg/day (therefore more than 100 times the effective dose) and after a 6-week treatment, the effects of IB 080 (and estriol) continue unchanged, whilst those of Premarin and estradiol decrease and/or inversed at 2nd or 4th week at doses that do not exceed the effective dose.

TABLE IV

Spontaneous lipaemia, Male, adult rats. Variations of the lipid parameters under the effect of several s.c. treatments at the uniform dose of 75 µg/kg/day.

| | | Controls day 0 (mg/ml) | Controls week (mg/ml) | Variations (%) in comparison with controls | | | |
|---|---|---|---|---|---|---|---|
| | | | | IB 080 | Premarin | $E_3$ | $E_2$ |
| 1st week | C | 1.09 | 1.12 | $-25^{ooo}$ | $-29^{ooo}$ | $-39^{ooo}$ | $-28^{ooo}$ |
| | TG | 1.04 | 0.50 | $-28$ | $-50^o$ | $-14$ | $-16$ |
| | TL | 3.37 | 3.46 | $-43^{ooo}$ | $-29^{ooo}$ | $-36^{ooo}$ | $-19^o$ |
| | PL | 1.77 | 1.87 | $-25.5^{5oo}$ | $-20^{ooo}$ | $-22^{ooo}$ | $-10^{oo}$ |
| 2nd week | C | — | 1.07 | $-43^{ooo}$ | $-3$ | $-35^{ooo}$ | $-6$ |
| | TG | — | 0.59 | $+32$ | $-44^o$ | $-10$ | $-3$ |
| | TL | — | 3.14 | $-35^{ooo}$ | $-15.5^o$ | $-33.5^{5ooo}$ | $-7$ |
| | PL | — | 1.48 | $-18.5^o$ | $-5.5$ | $-15$ | $-53^{ooo}$ |
| 3rd week | C | — | 1.04 | $-40^{ooo}$ | $-27^{ooo}$ | $-40^{ooo}$ | $+12$ |
| | TG | — | 0.89 | $+26$ | $-12$ | $+12$ | $+53.6^o$ |
| | TL | — | 5.55 | $-34.5^{5o}$ | $-20^{oo}$ | $-32^{ooo}$ | $+84^{ooo}$ |
| | PL | — | 2.03 | $-23.6^{ooo}$ | $-11.5^{oo}$ | $-13.5^o$ | $+46^{ooo}$ |
| 4th week | C | — | 0.965 | $-35^{ooo}$ | $-18^{ooo}$ | $-19^o$ | $+17^o$ |
| | TG | — | 0.46 | 0 | $+10$ | $+28^o$ | $+46$ |
| | TL | — | 2.85 | $-17^{oo}$ | $-7.6$ | $-14^o$ | $+31^{oo}$ |
| | PL | — | 1.50 | $-23.5^o$ | $-16.5^o$ | $-29.5^{oo}$ | $+47^{oo}$ |
| 5th week | C | — | 1.02 | $-52^{ooo}$ | 0 | $-52^{ooo}$ | 0 |
| | TG | — | 0.73 | $-13$ | $-35^{oo}$ | $-5$ | 0 |
| | TL | — | 3.49 | $-39^{ooo}$ | $-9$ | $-31^{oo}$ | $+18^{oo}$ |
| | PL | — | 1.58 | $-38^{ooo}$ | $-6$ | $-16^o$ | $+26^{oo}$ |
| 6th week | C | — | 0.965 | $-43^{ooo}$ | $-5$ | $-52^{ooo}$ | $+20^o$ |
| | TG | — | 0.51 | $-10$ | 0 | $+8$ | $-8$ |
| | TL | — | 2.77 | $-38^{ooo}$ | $-8$ | $-39^{ooo}$ | $+33^{ooo}$ |
| | PL | — | 1.30 | $-8$ | $+14^o$ | $-26^{oo}$ | $+41.5^{ooo}$ |

$^o = p<0.05$;
$^{oo} = p<0.01$;
$^{ooo} = p<0.001$

The interest of the avove in therapeutics is considerable the inversion of the effects of estrone, estradiol, its derivatives and Premarin and their negative consequences on human arteriosclerosis are well-known. This risk does not exist with estriol and the derivatives claimed by the present invention; further, the superiority of the latter over the estrogen of origin lies in the considerably enlarged therapeutic margin: at an identical antilipid effect (cf. Table II).

The basic of the invention and the usefulness of the claimed compounds in human therapeutics can be summarised as follows from all of the findings mentioned above:

1. The 16α,17β-nicotinic diesterification is responsible for the reinforcement of the original hypolipidaemic effects of estriol;

2. This reinforcement (cf. Table II) is patent with the trinicotinate ("IB 029") and the 3-cyclopentyl either ("IB 062"); It is revealed or reinforced by N-oxidation with the other compounds:
   from 62% to 1300% between "IB 032 and its N-oxide, "IB 080"
   from 100% to 1600% between "IB 113" and its N-oxide, "IB 101",
   from 580% to 1700% between "IB 029" and its N-oxide, "IB 056".

3. Two other consequences of the N-oxidation are:
   a. the reduction in the estrogenic effects in general,
   b. which reduction affects the s.c. activity more than the oral activity.

4. The corollary of the above is the increase of the range between the hypolipidaemic effect of the N-oxides and their estrogenic effects (greatly diminished).

Thus for instance, compound "IB 080" at a given dose, is 240 to 380 times more hypolipidaemic than estrogenic, whereas its non N-oxidated homologue ("IB 032") is only 12 times, under the best conditions. This N-oxidation effect is confirmed with the other derivatives (see Table II).

5. The estrogenic effects are modulated, according to the present invention, by the nature of the substitution at $C_{(3)}$: the claimed hypolipidaemic compounds thus enable the practitioners to choose according to whether the patient fears the hormonal effect, or whether he needs it and, in this case, according to his specific needs.

To conclude, the nicotinic derivatives of estriol, according to the invention, are useful in human therapeutics, due to the modifications of the biological outline of the original steroid (estriol) by the various chemical modifications specified in this invention: 16α, 17βnicotinic diesterification; the nature of the substitution at the phenol hydroxyl; existence or not of the N-oxidation.

Thus, all these compounds are more hypolipidaemic than estriol; the N-oxidated nicotinic diesters are far more hypolipidaemic and this, not only in absolute but in relative value also since the estrogenic effets are electively decreased by the N-oxidation; they all maintain the exclusive characteristic of estriol which is the absence of the inversion of effects, even at high doses and after prolonged treatment.

The therapeutical applications of the compounds relating to this invention can take the usual various routes: oral or perlingual; parenteral (e.g. intramuscular); rectal transcutaneous.

The vehicle will be chosen according to the route of administration and the excipient must be pharmaceutically acceptable: sterile, injectable solutions or suspensions; or adsorption on, or a mixture in an acceptable excipient, in the form of tablets, capsules suppositories, lipid or volatile solutions, creams ointments, gels etc.

The above-named units, cited as examples, will contain a quantity of product between 1 mg and 10 mg according to the compound and therapeutical indication concerned (see below). Thus:

1. as estrogenic substitution in women with hyperlipidaemic history or high vascular risk, it is preferable to use compounds IB 031, IB 062 and IB 029 (by the injectable rectal or transcutaneous routes), IB 062 or IB 104 (by the oral or perlingual routes), the daily dosage varying according to the case, from 1 mg to 8 mg/day.

2. as estrogenic substitution in women with patent hyperlipidaemia, it is preferable to use compound IB 056, whatever the route choosen, the daily dose varying from 2 mg to 10 mg.

3. as a hypolipidaemic and anti-arteriosclerosis treatment in both sexes, it is preferable to use IB 080, whatever the route chosen, the dose varying according to the case, from 1 mg to 10 mg.

I claim:

1. The compound 3-methoxy-16α,17β-dinicotinoyloxy-1,3,5(10)-estratriene.

2. The compound 3-cyclopentyloxy-16α,17β-dinicotinoyloxy-1,3,5(10)-estratriene.

3. The compound 3-cyclopentyloxy-16α,17β-dinicotinoyloxy-1,3,5(10)-estratriene-di-N-oxide.

* * * * *